(12) United States Patent
Reid et al.

(10) Patent No.: US 12,300,213 B2
(45) Date of Patent: May 13, 2025

(54) NOISE CONTROL

(71) Applicant: Dyson Technology Limited, Wiltshire (GB)

(72) Inventors: Peter Knight Reid, Swindon (GB); Philip Stephen Darling, Bristol (GB)

(73) Assignee: Dyson Technology Limited, Wiltshire (GB)

( * ) Notice: Subject to any disclaimer, the term of this patent is extended or adjusted under 35 U.S.C. 154(b) by 282 days.

(21) Appl. No.: 17/418,184

(22) PCT Filed: Dec. 17, 2019

(86) PCT No.: PCT/GB2019/053575
§ 371 (c)(1),
(2) Date: Jun. 24, 2021

(87) PCT Pub. No.: WO2020/157447
PCT Pub. Date: Aug. 6, 2020

(65) Prior Publication Data
US 2022/0148557 A1  May 12, 2022

(30) Foreign Application Priority Data
Jan. 31, 2019 (GB) ..................................... 1901349

(51) Int. Cl.
*G10K 11/178* (2006.01)
*A61F 11/14* (2006.01)
(Continued)

(52) U.S. Cl.
CPC ...... *G10K 11/17854* (2018.01); *A61F 11/145* (2022.01); *A62B 18/003* (2013.01);
(Continued)

(58) Field of Classification Search
CPC .......... G10K 2210/1081; H04R 1/1083; H04R 2410/05
See application file for complete search history.

(56) References Cited

U.S. PATENT DOCUMENTS

| 8,447,045 B1 | 5/2013 | Laroche |
| 2003/0188743 A1 | 10/2003 | Manne |

(Continued)

FOREIGN PATENT DOCUMENTS

| CN | 201292994 Y | 8/2009 |
| CN | 102473407 A | 5/2012 |

(Continued)

OTHER PUBLICATIONS

Machine translation of KR 101796969 B1, 12 pages. (Year: 2017).*
(Continued)

*Primary Examiner* — Ping Lee
(74) *Attorney, Agent, or Firm* — Tucker Ellis LLP

(57) ABSTRACT

There is provided an ear cup comprising a housing, an ear pad attached to the housing and arranged such that the housing and the ear pad together define a cavity having an opening, and an acoustic driver disposed within the cavity. The ear cup further comprises a feedforward microphone, a feedback microphone, and active noise control (ANC) circuitry. The active noise control (ANC) circuitry is configured to use a feedforward signal provided by the feedforward microphone to operate the acoustic driver to attenuate noise having frequencies within a feedforward ANC range having a lower limit of no less than 300 Hz and an upper limit of more than 1.5 kHz and to use a feedback signal provided by the feedback microphone to operate the acoustic driver to attenuate noise having frequencies within a feedback ANC range having an upper limit of no more than 1.5 kHz.

20 Claims, 9 Drawing Sheets

(51) Int. Cl.
A62B 18/00 (2006.01)
B01D 46/00 (2022.01)
B01D 46/44 (2006.01)
H04R 1/10 (2006.01)

(52) U.S. Cl.
CPC ......... *B01D 46/0043* (2013.01); *B01D 46/44* (2013.01); *G10K 11/17823* (2018.01); *G10K 11/17825* (2018.01); *G10K 11/17881* (2018.01); *H04R 1/1008* (2013.01); *H04R 1/1075* (2013.01); *B01D 2273/30* (2013.01); *G10K 2210/1081* (2013.01); *G10K 2210/3026* (2013.01); *G10K 2210/3027* (2013.01); *G10K 2210/3028* (2013.01); *H04R 2460/01* (2013.01)

(56) References Cited

U.S. PATENT DOCUMENTS

| | | |
|---|---|---|
| 2004/0194776 A1 | 10/2004 | Amir |
| 2004/0264706 A1 | 12/2004 | Ray et al. |
| 2005/0249355 A1 | 11/2005 | Chen et al. |
| 2010/0272283 A1 | 10/2010 | Carreras et al. |
| 2011/0044464 A1 | 2/2011 | Sapiejewski et al. |
| 2014/0051483 A1 | 2/2014 | Schoerkmaier |
| 2014/0086425 A1 | 3/2014 | Jensen et al. |
| 2014/0126734 A1 | 5/2014 | Gauger, Jr. et al. |
| 2014/0126735 A1 | 5/2014 | Gauger, Jr. |
| 2015/0296297 A1 | 10/2015 | Hua et al. |
| 2017/0148428 A1* | 5/2017 | Thuy .................. H04R 1/1083 |
| 2019/0069074 A1 | 2/2019 | Yamkovoy |
| 2022/0180850 A1 | 6/2022 | Reid et al. |
| 2022/0180851 A1 | 6/2022 | Reid et al. |
| 2022/0182749 A1 | 6/2022 | Reid et al. |

FOREIGN PATENT DOCUMENTS

| | | |
|---|---|---|
| CN | 103052851 A | 4/2013 |
| CN | 103949017 A | 7/2014 |
| CN | 103961822 A | 8/2014 |
| CN | 103994485 A | 8/2014 |
| CN | 203775388 U | 8/2014 |
| CN | 203852759 U | 10/2014 |
| CN | 203898976 U | 10/2014 |
| CN | 105120391 A | 12/2015 |
| CN | 105571010 A | 5/2016 |
| CN | 105999576 A | 10/2016 |
| CN | 106454576 A | 2/2017 |
| CN | 206713019 U | 12/2017 |
| CN | 206922999 U | 1/2018 |
| CN | 107750026 A | 3/2018 |
| CN | 107750028 A | 3/2018 |
| CN | 108696785 A | 10/2018 |
| CN | 207968819 U | 10/2018 |
| CN | 208536174 U | 2/2019 |
| CN | 211860491 U | 11/2020 |
| CN | 212411572 U | 1/2021 |
| CN | 212413389 U | 1/2021 |
| CN | 212413390 U | 1/2021 |
| DE | 102017129469 | 6/2019 |
| EP | 1074971 | 2/2001 |
| EP | 2594853 A1 | 5/2013 |
| EP | 2602566 A1 | 6/2013 |
| GB | 2434708 A | 8/2007 |
| GB | 2441835 | 3/2008 |
| GB | 2487125 | 7/2012 |
| JP | 01-251214 A | 10/1989 |
| JP | 2016-061534 A | 4/2016 |
| JP | 2022-528484 A | 6/2022 |
| JP | 2022-528624 A | 6/2022 |
| JP | 2022-529101 A | 6/2022 |
| KR | 10-2009-0035888 A | 4/2009 |
| KR | 10-2009-0115450 A | 11/2009 |
| KR | 10-1796969 B1 | 11/2017 |
| KR | 10-1889372 B1 | 8/2018 |
| KR | 20-0488413 Y1 | 1/2019 |
| WO | 2009/134107 A2 | 11/2009 |
| WO | 2013/082650 | 6/2013 |
| WO | 2016/047069 | 3/2016 |
| WO | 2017/120992 A1 | 7/2017 |
| WO | 2019/050849 A1 | 3/2019 |
| WO | 2020/193936 A1 | 10/2020 |
| WO | 2020/193937 A1 | 10/2020 |
| WO | 2020/193938 A1 | 10/2020 |

OTHER PUBLICATIONS

Office Action received for Chinese Patent Application No. 202010198931.2, mailed on Jun. 15, 2022, 18 pages (10 pages of English Translation and 8 pages of Original Document).
Office Action received for Chinese Patent Application No. 202010198997.1, mailed on Jun. 15, 2022, 22 pages (12 pages of English Translation and 10 pages of Original Document).
Office Action received for Japanese Patent Application No. 2021-556860, mailed on Nov. 22, 2022, 7 pages (4 pages of English Translation and 3 pages of Original Document).
Office Action received for Japanese Patent Application No. 2021-556871, mailed on Nov. 22, 2022, 6 pages (3 pages of English Translation and 3 pages of Original Document).
International Search Report and Written Opinion received for PCT Patent Application No. PCT/GB2020/050440, mailed on May 14, 2020, 12 pages.
Office Action received for Chinese Patent Application No. 202010198915.3, mailed on Apr. 26, 2022, 24 pages (12 pages of English Translation and 12 pages of Original Document).
Evaluation Report received for CN Application No. 202020367425. 7, mailed on Dec. 14, 2020, 5 pages (Original Document Only).
Evaluation Report received for CN Application No. 202020367431. 2, mailed on Jul. 23, 2021, 4 pages (Original Document Only).
GB Search Report received for GB App. No. 1903969, mailed on Jun. 3, 2019, 2 pages.
GB Search Report received for GB Application No. 1903971, mailed on May 29, 2019, 2 pages.
International Search Report and Written Opinion received for PCT Patent Application No. PCT/GB2020/050441, mailed on May 19, 2020, 11 pages.
International Search Report and Written Opinion received for PCT Patent Application No. PCT/GB2020/050442, mailed on May 20, 2020, 12 pages.
Office Action received for CN Application No. 202020367425.7, mailed on Apr. 20, 2021, 3 pages (Original Document Only).
Evaluation Report dated Mar. 19, 2021, directed to CN Application No. ZL2020201409149; 9 pages.
International Search Report and Written Opinion mailed Mar. 5, 2020, directed to International Application No. PCT/GB2019/053575; 9 pages.
Search Report dated Apr. 15, 2019, directed to GB Application No. 1901349.9; 2 pages.
Office Action received for Korean Patent Application No. 10-2021-7033884, mailed on May 17, 2023, 19 pages (10 pages of English Translation and 09 pages of Original Document).
Office Action received for Korean Patent Application No. 10-2021-7034206, mailed on May 17, 2023, 22 pages (11 pages of English Translation and 11 pages of Original Document).
Office Action received for Korean Patent Application No. 10-2021-7034207, mailed on Jun. 21, 2023, 16 pages (7 pages of English Translation and 9 pages of Original Document).
Office Action received for Japanese Patent Application No. 2021-556860, mailed on Jul. 4, 2023, 8 pages (5 pages of English Translation and 3 pages of Original Document).
Office Action received for Korean Patent Application No. 10-2021-7024039, mailed on Oct. 20, 2023, 17 pages (8 pages of English Translation and 9 pages of Original Document).
Office Action received for Chinese Patent Application No. 202010069293.4, mailed on Dec. 6, 2023, 28 pages (16 pages of English Translation and 12 pages of Original Document).

* cited by examiner

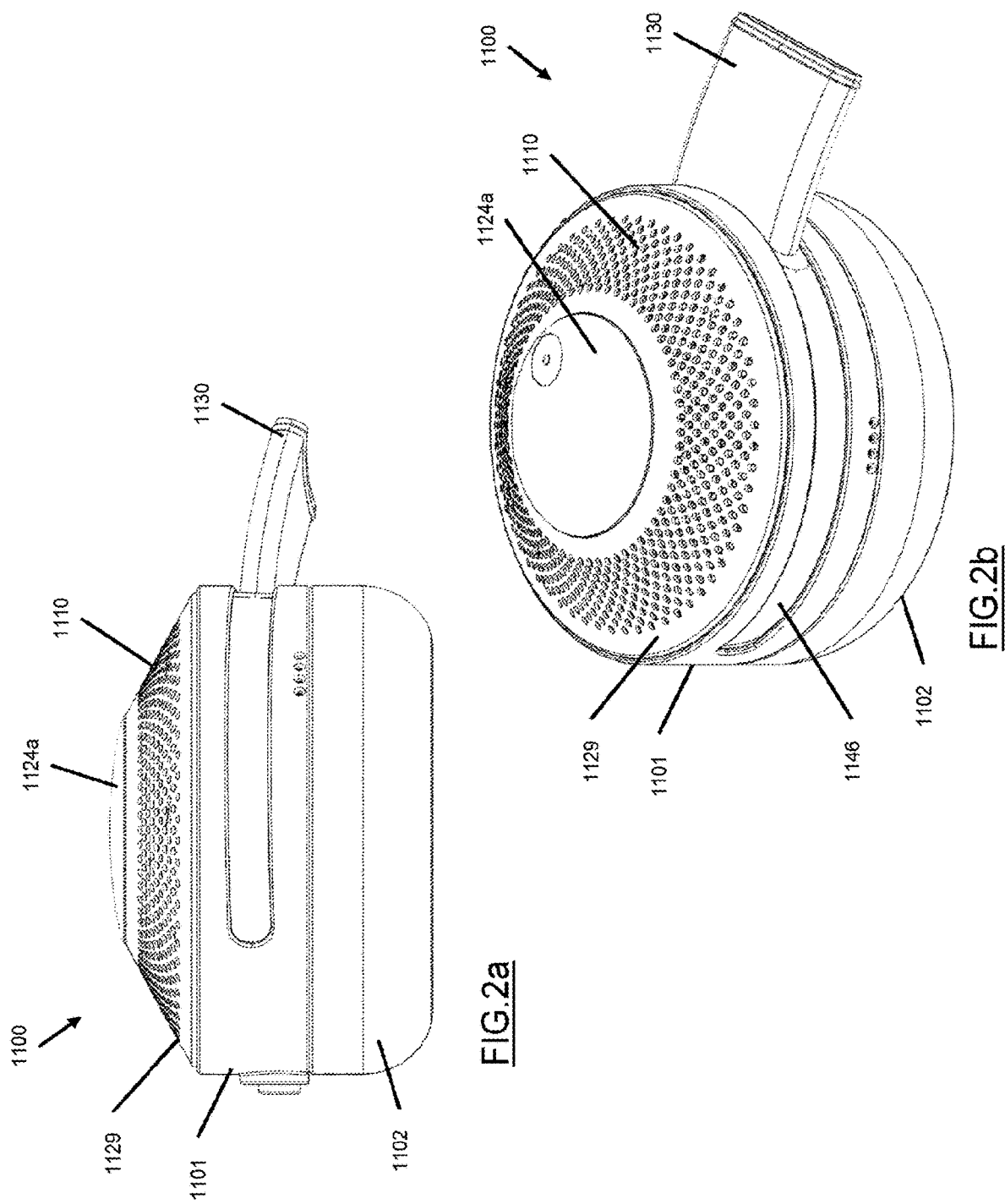

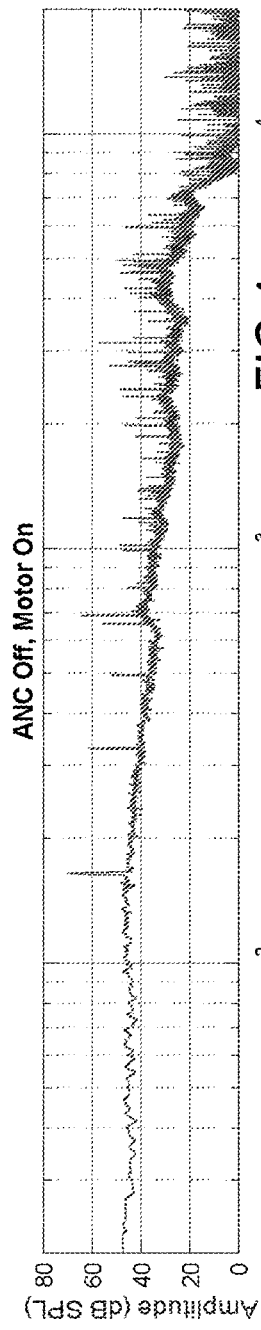
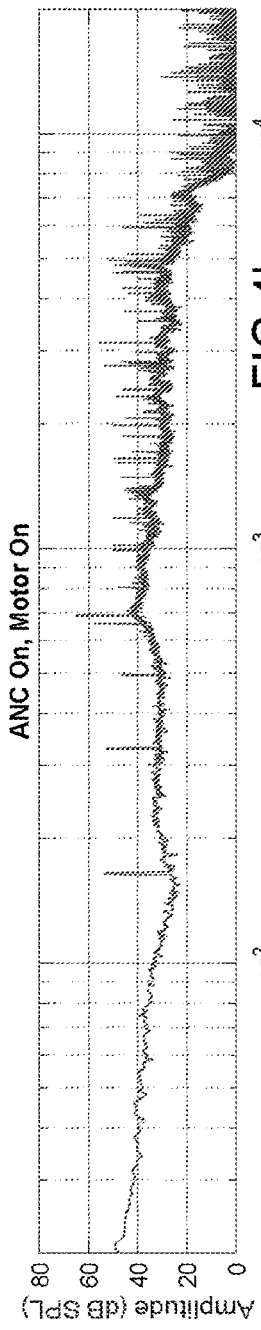
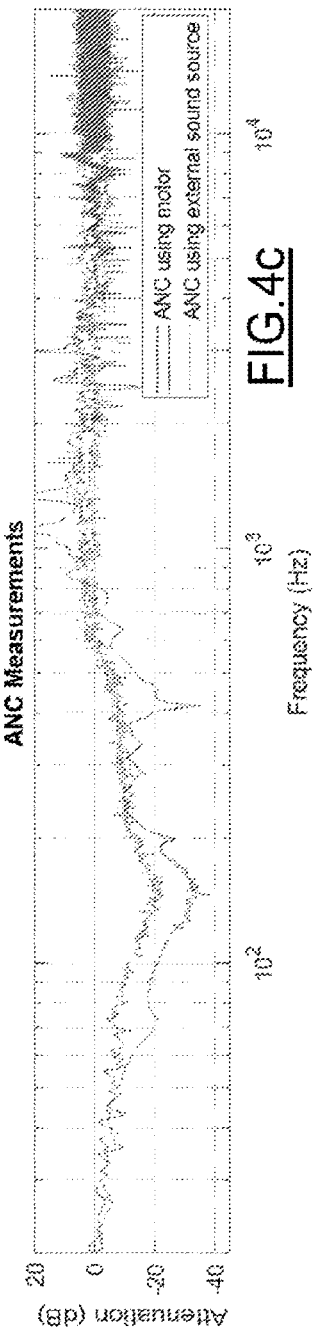

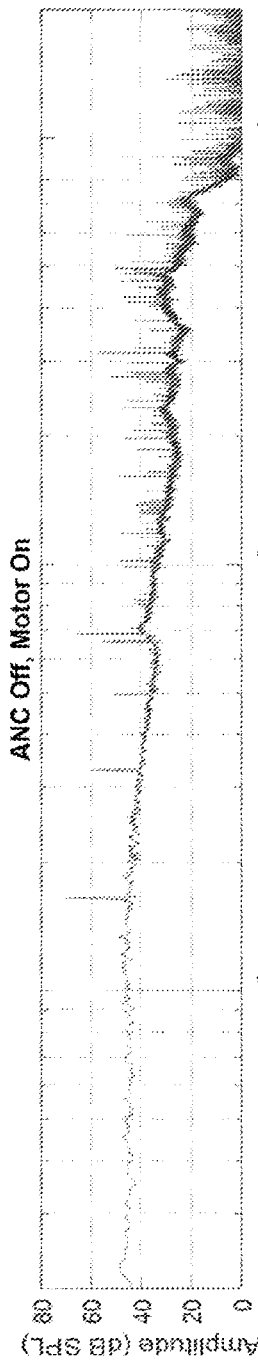
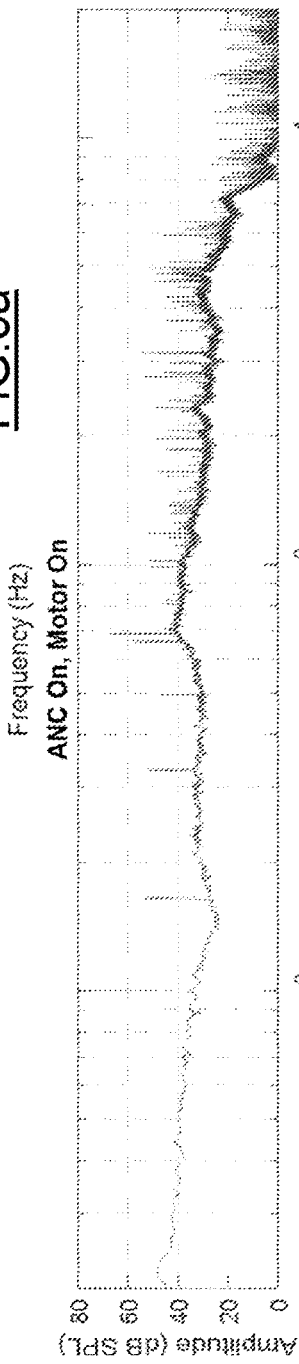
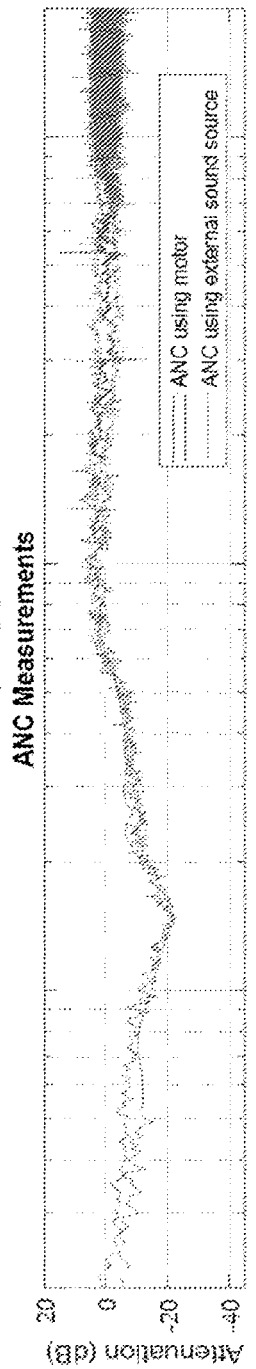

NOISE CONTROL

REFERENCE TO RELATED APPLICATIONS

This application is a national stage application under 35 U.S.C. 371 of International Application No. PCT/GB2019/053575, filed Dec. 17, 2019, which claims the benefit of United Kingdom Application No. 1901349.9, filed Jan. 31, 2019, the entire contents of each of which are incorporated herein.

FIELD OF THE DISCLOSURE

The present invention relates to noise control in an ear cup or speaker assembly, and specifically relates to an implementation of active noise control within the ear cup of a head wearable air purifier.

BACKGROUND OF THE DISCLOSURE

Air pollution is an increasing problem and a variety of air pollutants have known or suspected harmful effects on human health. The adverse effects that can be caused by air pollution depend upon the pollutant type and concentration, and the length exposure to the polluted air. For example, high air pollution levels can cause immediate health problems such as aggravated cardiovascular and respiratory illness, whereas long-term exposure to polluted air can have permanent health effects such as loss of lung capacity and decreased lung function, and the development of diseases such as asthma, bronchitis, emphysema, and possibly cancer.

In locations with particularly high levels of air pollution, many individuals have recognised the benefits of minimising their exposure to these pollutants and have therefore taken to wearing face masks with the aim of filtering out at least a portion of the pollutants present in the air before it reaches the mouth and nose. These face masks range from basic dust masks that merely filter out relatively large dust particles, to more complex air-purifying respirators that require that the air pass through a filter element or cartridge. However, as these face masks typically cover at least the users mouth and nose they can make normal breathing more laborious and can also cause problems with the user's ability to speak to others, such that there is some reluctance to make use of such face masks on a day-to-day basis despite the potential benefits.

As a consequence, there have been various attempts to develop air purifiers that can be worn by the user but that do not require the user's mouth and nose to be covered. For example, there are various designs for wearable air purifiers that are worn around the neck of the user and that create a jet of air that is directed upwards towards the user's mouth and nose. Whilst these may be more socially acceptable, they are generally less effective at limiting the user's exposure to airborne pollutants than some of the best performing face-worn filters. This is largely due to the lack of accuracy with which they deliver the jet of air to the user's mouth and nose and to the fact that flows of unfiltered air that can still reach the user's mouth and nose.

WO2017120992, CN103949017A, KR101796969B1 and CN203852759U all describe head-worn purifiers that provide an alternative to both face masks and neck-worn purifiers. WO2017120992 describes a system in which a separate air filtering unit is connected by a pipe to an air outlet provided on an arm that extends from one of the earphones. Each of CN103949017A, KR101796969B1 and CN203852759U then describe headsets in which both a fan and a filter are incorporated into at least one of the ear cups. Of these, only KR101796969B1 considers implementing active noise control (ANC) to reduce the noise generated by the air supply unit. Specifically, KR101796969B1 states that the ear cup is provided with a frequency generator that generates a frequency for cancelling the noise of the air supply unit, and that this can be achieved using conventional techniques for noise reduction. However, contrary to this assertion, implementing active noise control to attenuate noise generated by a fan located within an ear cup is not straightforward.

Active noise control uses destructive interference to attenuate noise. The frequency, amplitude and phase of any undesired sound are identified and another sound of the same frequency and amplitude but opposite phase is created, i.e. an 'anti-noise' sound, with the intention that this 'anti-noise' sound will cancel out the noise. Within a headset, the anti-noise signal is combined with the desired audio signal before being output by the audio transducer.

Active noise control can be implemented using any of a feedforward, a feedback or a hybrid system. In a feedforward system, a reference noise microphone, referred to as a feedforward microphone, is located close to the exterior of the headset to directly measure the noise from the environment and provide this measurement as an input to a feedforward ANC filter. The feedforward ANC filter then uses the input from the feedforward microphone to generate an anti-noise signal that aims to attenuate the measured noise. In a feedback system, an error noise microphone, referred to as a feedback microphone, is located close to the user's ear, typically adjacent to the acoustic transducer, to measure the sounds that are heard by the user and provide this measurement as an input to a feedback ANC filter. The feedback ANC filter then compares the input from the feedback microphone with desired audio source to identify unwanted noise and generates an anti-noise signal with the aim of attenuating the identified noise. A hybrid system then combines both a feedforward system and a feedback system to improve the overall noise cancellation performance In particular, in advanced hybrid systems the feedforward system and the feedback system do not function entirely independently of one another, as the noise identified by the feedback system is used to improve the performance of the feedforward ANC filter (i.e. is used as an input for determining the coefficients of the feedforward ANC filter).

In conventional headsets active noise control is only required to cancel noise that is generated externally. However, in a head-worn purifier in which a fan is located within an ear cup, noise will also be produced internally by the motor that drives the fan and by the rush of air entering the headset. Conventionally configured ANC systems cannot attenuate both the external environmental (i.e. exogenous) noise and the internally originating (i.e. endogenous) noise.

SUMMARY OF THE DISCLOSURE

It is an object of the present invention to provide an ear cup, and a head wearable air purifier comprising the ear cup, in which active noise control is capable of attenuating both external environmental (i.e. exogenous) noise and internally originating (i.e. endogenous) noise.

According to a first aspect of the present invention there is provided an ear cup comprising a housing, an ear pad attached to the housing and arranged such that the housing and the ear pad together define a cavity having an opening, and an acoustic driver disposed within the cavity. The ear cup further comprises a feedforward microphone (i.e. a reference noise microphone) carried by the housing and acoustically coupled to the environment external to the housing, an feedback microphone (i.e. an error noise microphone) disposed within the cavity, and active noise control (ANC) circuitry. The active noise control (ANC) circuitry is configured to use a feedforward signal provided by the feedforward microphone to operate the acoustic driver to attenuate noise having frequencies within a feedforward ANC range having a lower limit of at least (i.e. no less than) 300 Hz and an upper limit of more than 1.5 kHz and to use a feedback signal provided by the feedback microphone to operate the acoustic driver to attenuate noise having frequencies within a feedback ANC range having an upper limit of no more than 1.5 kHz.

Within conventional headsets, feedforward ANC systems are typically configured to attenuate noise have frequencies below 2 kHz and specifically noise having frequencies within the range of 40 Hz to 1.5 kHz, whilst conventional feedback ANC systems are typically configured to attenuate noise have frequencies within the range of 20 Hz to 500 Hz. In contrast, the present inventors have found that, whilst the motor within a head wearable air purifier can be configured such that the fundamental frequency of the motor noise is attenuated by a conventionally configured feedback ANC system, attenuation of additional endogenous noise (e.g. higher harmonics of the motor noise, air rush noise etc.) requires a feedforward ANC system whose resources are applied in a completely different way to conventional ANC headsets.

The active noise control circuitry may comprise a feedforward filter that is configured to receive the feedforward signal as an input and to generate a feedforward filter output that causes the acoustic driver to attenuate noise having frequencies within the feedforward ANC range.

The lower limit of the feedforward ANC range may be at least (i.e. no less than) 350 Hz. The lower limit of the feedforward ANC range may be approximately 500 Hz. The upper limit of the feedforward ANC range may be at least (i.e. no less than) 2 kHz. The upper limit of the feedforward ANC range may be approximately 2 kHz. The lower limit of the feedforward ANC range may be approximately 500 Hz and the upper limit approximately 2 kHz.

The active noise control circuitry may comprise a feedback filter that is configured to receive the feedback signal as an input and to generate a feedback filter output that causes the acoustic driver to attenuate noise having frequencies within the feedback ANC range.

The upper limit of the feedback ANC range may be approximately 500 Hz. The lower limit of the feedback ANC range may be at least (i.e. no less than) 20 Hz, and may be approximately 50 Hz. The lower limit of the feedback ANC range may be approximately 50 Hz and the upper limit approximately 500 Hz.

The ear cup may further comprise a motor-driven impeller disposed within the housing, wherein the motor-driven impeller is arranged to create an airflow through the housing. The ear cup may further comprise a control circuit arranged to control a rotational speed of the motor-driven impeller such that the maximum rotational speed of the motor-driven impeller is from 9000 to 18,000 RPM. The control circuit may be arranged to control a rotational speed of the motor-driven impeller such that the maximum rotational speed of the motor-driven impeller is from 10,000 to 14,000 RPM, and is preferably from 10,000 to 12,000 RPM.

The housing may comprise an air inlet through which an airflow can be drawn into the housing by the motor-driven impeller and an air outlet for emitting the airflow from the housing. The ear cup may further comprise a filter assembly disposed within the housing, wherein the motor-driven impeller is arranged to create an airflow through the filter assembly. The air outlet of the housing may be downstream from the filter assembly.

According to a second aspect of the present invention there is provided an ear cup comprising a housing, an ear pad attached to the housing and arranged such that the housing and the ear pad together define a cavity having an opening, and an acoustic driver disposed within the cavity. The ear cup further comprises a feedback microphone (i.e. an error noise microphone) disposed within the cavity, a feedforward microphone (i.e. a reference noise microphone) carried by the housing and acoustically coupled to the environment external to the housing, and active noise control circuitry. The active noise control circuitry is configured to use a feedback signal provided by the feedback microphone to operate the acoustic driver to attenuate noise having frequencies within a feedback ANC range and that is further configured to use a feedforward signal provided by the feedforward microphone to operate the acoustic driver to attenuate noise having frequencies within a feedforward ANC range, wherein the feedback ANC range does not overlap with the feedforward ANC range.

Conventional hybrid ANC systems use both the feedforward ANC system and the feedback ANC system to deal with low frequency noise (e.g. 100-500 Hz) such that they are intentionally configured to overlap the attenuation provided by the feedforward ANC system and the feedback ANC system. In contrast, the present inventors have found that, whilst the motor within a head wearable air purifier can be configured such fundamental frequency of the motor noise can be attenuated by a conventionally configured feedback ANC system, the feedforward ANC system should be targeted at the higher frequency air rush noise and overtones of the motor noise. Furthermore, the response of the feedforward ANC system should not result in undesirable amplification of the endogenous noise. Consequently, in such a system it is desirable that the feedback ANC system and the feedforward ANC system are configured such that their responses do not overlap.

The active noise control circuitry may comprise a feedback filter that is configured to receive the feedback signal as an input and to generate a feedback filter output that causes the acoustic driver to attenuate noise having frequencies within the feedback ANC range. The active noise control circuitry may further comprise a feedforward filter that is configured to receive the feedforward signal as an input and to generate a feedforward filter output that causes the acoustic driver to attenuate noise having frequencies within the feedforward ANC range.

The ear cup may be configured as any of a circumaural ear cup and a supra-aural ear cup, and is preferably configured as a circumaural ear cup.

According to a third aspect of the present invention there is provided a head wearable device comprising a headgear, and an ear cup as defined in any of the first aspect and the second aspect, wherein the ear cup is attached to the headgear and is arranged to be worn over an ear of a user.

The head wearable device may further comprise a further ear cup arranged to be worn over a further ear of the user. The further ear cup may be as defined in any of the first aspect and the second aspect. The headgear may comprise a headband arranged to be worn on the head of a user. The ear cup may then be mounted on a first end of the headband and the further ear cup mounted on an opposite, second end of the headband.

According to another aspect there is also provided active noise control (ANC) circuitry that is configured to receive a feedforward signal and to use the feedforward signal to generate instructions for an acoustic driver to attenuate noise having frequencies within a feedforward ANC range having a lower limit of at least (i.e. no less than) 300 Hz and an upper limit of more than 1.5 kHz. The active noise control (ANC) circuitry may be configured to receive the feedforward signal from a feedforward microphone. The active noise control (ANC) circuitry may be configured to send the instructions to an acoustic driver.

According to another aspect there is also provided a method of implementing active noise control (ANC). The method comprises receiving a feedforward signal from a feedforward microphone and using the feedforward signal to generate instructions for an acoustic driver to attenuate noise having frequencies within a feedforward ANC range having a lower limit of at least (i.e. no less than) 300 Hz and an upper limit of more than 1.5 kHz. The method may further comprise sending the instructions to an acoustic driver.

According to a further aspect there is also provided active noise control (ANC) circuitry that is configured to receive both a feedback signal and a feedforward signal. The active noise control (ANC) circuitry is further configured to use the feedback signal to generate instructions for an acoustic driver to having frequencies within a feedback ANC range, and to use the feedforward signal to generate instructions for the acoustic driver to attenuate noise having frequencies within a feedforward ANC range, wherein the active noise control (ANC) circuitry is configured such that the feedback ANC range does not overlap with the feedforward ANC range. The active noise control (ANC) circuitry may be configured to receive the feedback signal from a feedback microphone. The active noise control (ANC) circuitry may be configured to receive the feedforward signal from a feedforward microphone. The active noise control (ANC) circuitry may be configured to send the instructions to an acoustic driver.

According to a yet further aspect there is also provided a method of implementing active noise control (ANC). The method comprises receiving both a feedback signal and a feedforward signal, using the feedback signal to generate instructions for an acoustic driver to having frequencies within a feedback ANC range, and using the feedforward signal to generate instructions for the acoustic driver to attenuate noise having frequencies within a feedforward ANC range, wherein the feedback ANC range does not overlap with the feedforward ANC range. The method may further comprise receiving the feedback signal from a feedback microphone. The method may further comprise receiving the feedforward signal from a feedforward microphone. The method may further comprise sending the instructions to an acoustic driver.

BRIEF DESCRIPTION OF THE FIGURES

An embodiment of the present invention will now be described, by way of example only, with reference to the accompanying drawings, in which:

FIG. 1b is a front view of the head wearable air purifier of FIG. 1a;

FIG. 2a is a side view of an ear cup of the head wearable air purifier of FIG. 1a;

FIG. 2b is a perspective view of the ear cup of FIG. 2a;

FIG. 3a is a cross-sectional view through the speaker assembly of FIG. 2a;

FIG. 3b is a further cross-sectional view through the speaker assembly of FIG. 2a;

FIG. 4a is a graph showing sound measurements taken for a head wearable purifier such as that described herein without any active noise control;

FIG. 4b is a graph showing sound measurements taken for a head wearable purifier such as that described herein with hybrid active noise control;

FIG. 4c is a graph comparing the attenuation achieved by hybrid active noise control on the internally originating noise with the attenuation achieved by the hybrid active noise control on externally originating noise;

FIG. 5a is a graph showing sound measurements taken for a head wearable purifier such as that described herein without any active noise control;

FIG. 5b is a graph showing sound measurements taken for a head wearable purifier such as that described herein with feedback only active noise control;

FIG. 5c is a graph comparing the attenuation achieved by feedback only active noise control on the internally originating noise with the attenuation achieved by the feedback only active noise control on externally originating noise.

DETAILED DESCRIPTION OF THE DISCLOSURE

There will now be described an ear cup, and a head wearable air purifier comprising the ear cup, in which active noise control is capable of attenuating both external environmental (i.e. exogenous) noise and internally originating (i.e. endogenous) noise. The term "air purifier" as used herein refers to a device or system capable of removing contaminants from air and emitting a supply of purified or filtered air. The term "head wearable" is used herein to define an item as being capable of or suitable for being worn on the head of a user.

The term "headphones" as used herein refers to a pair of small loudspeakers, or speakers, joined by a headband that is designed to be worn on or around the head of a user. Typically, the speakers are provided by electroacoustic transducers that convert an electrical signal to a corresponding sound. Circumaural headphones, often referred to as full-size or over-ear headphones, have ear pads whose shape is that of a closed loop (e.g. circular, elliptical etc.) so that they encompass the entire ear. Because these headphones completely surround the ear, circumaural headphones can be designed to fully seal against the head to attenuate external noise. Supra-aural headphones, often referred to as on-ear headphones, have ear pads that press against the ears, rather than around them. This type of headphone generally tends to be smaller and lighter than circumaural headphones, resulting in less attenuation of outside noise.

Figure 1A:
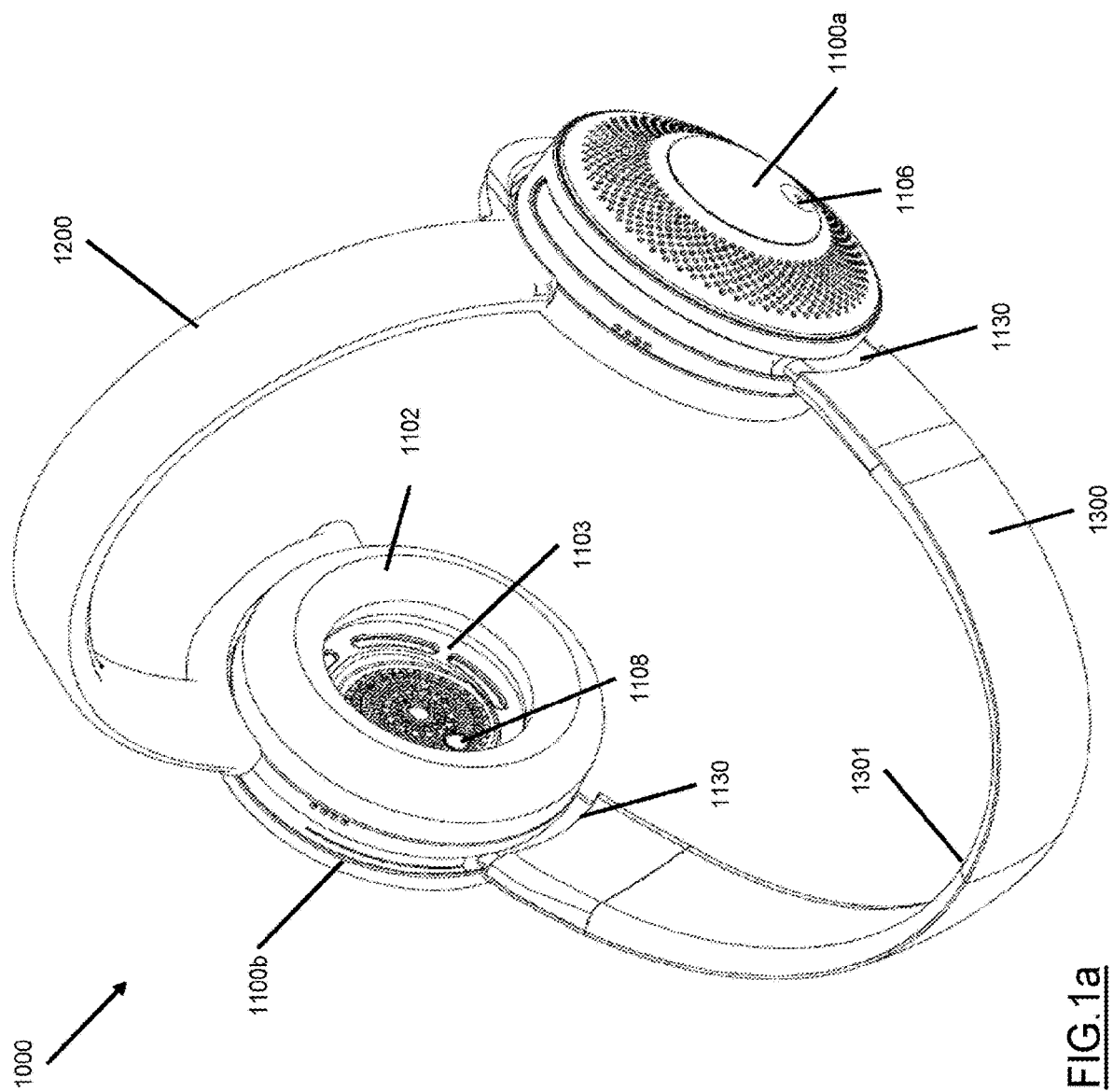
FIG. 1a is a front perspective view of an embodiment of a head wearable air purifier as described herein.
Figure 1B:
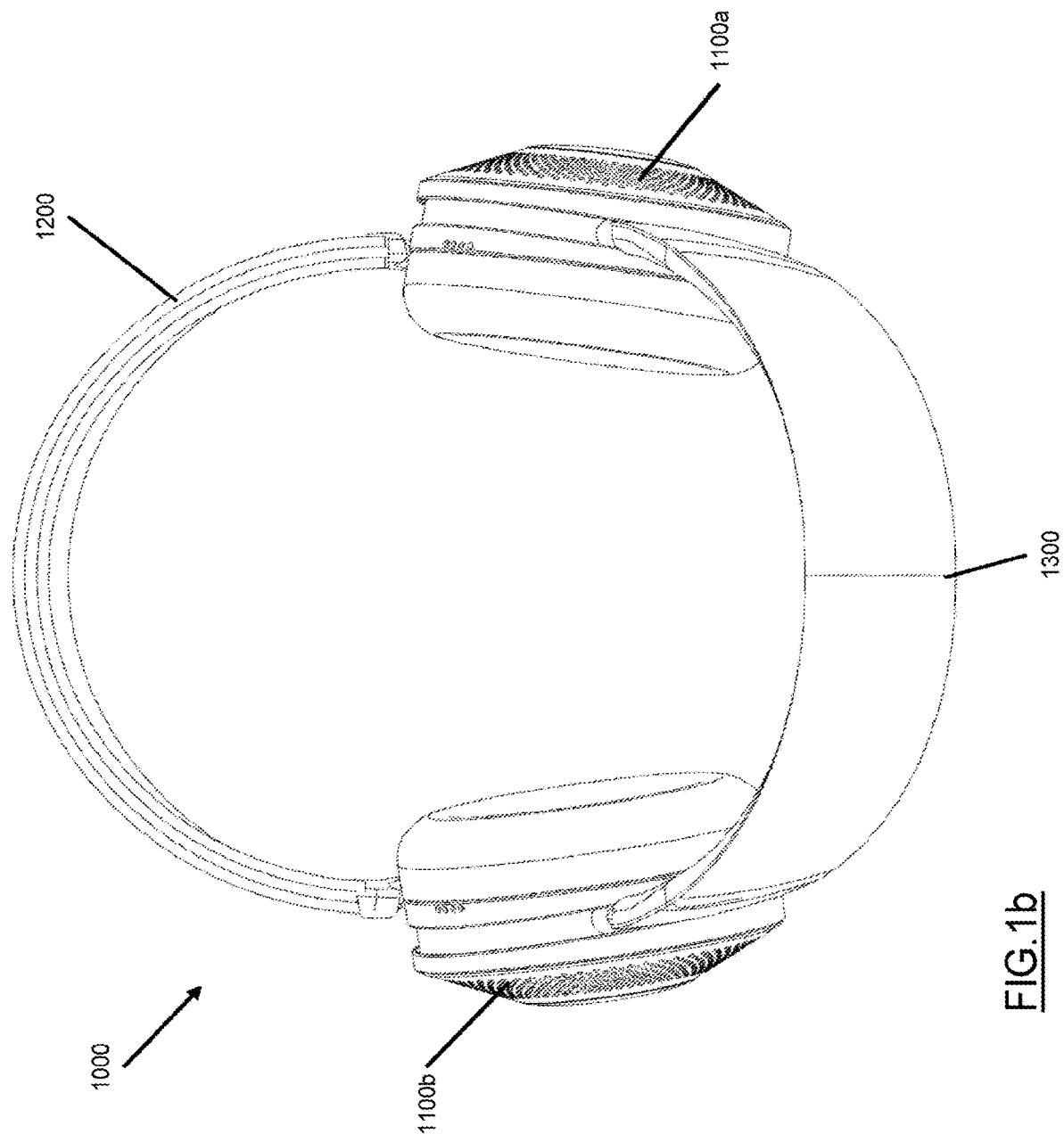
Figure 3A:
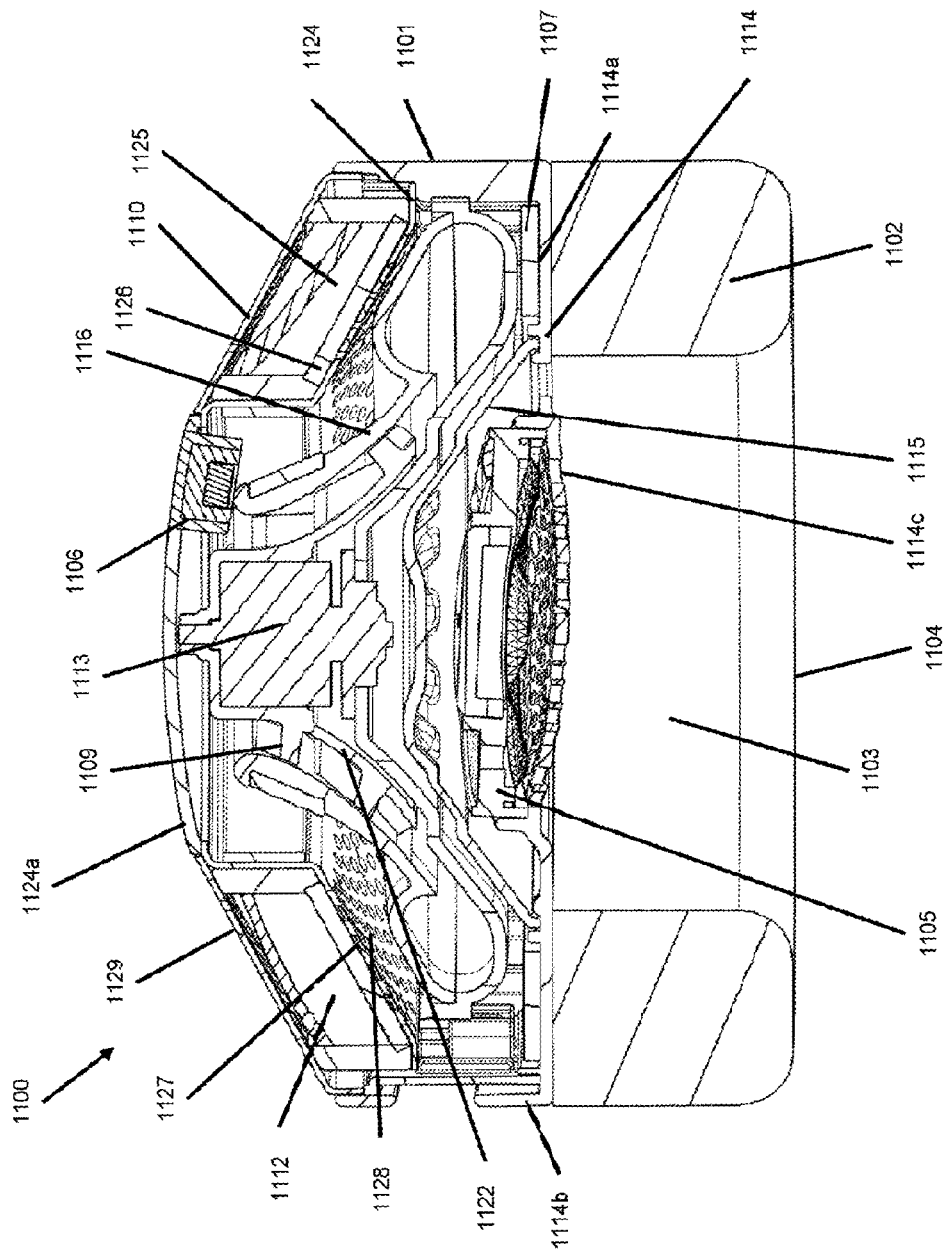
Figure 3B:
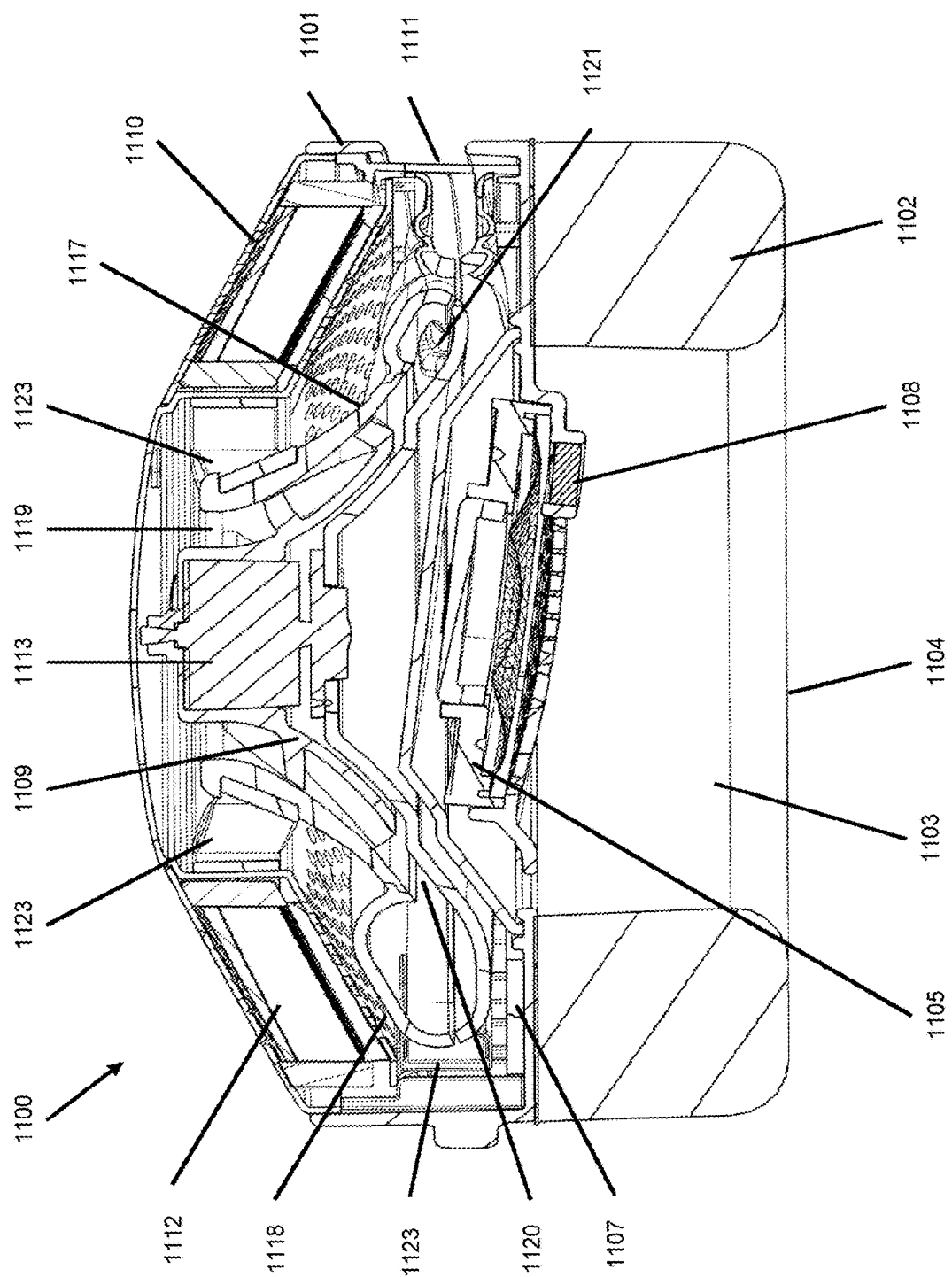

FIGS. 1a and 1b are external views of an embodiment of a head wearable air purifier 1000. The head wearable air purifier 1000 comprises a pair of generally cylindrical ear cups or speaker assemblies 1100a, 1100b connected by an arcuate headband 1200, and a nozzle 1300 that extends between and is connected at opposite ends to both ear cups 1100a, 1100b. FIG. 2a then shows a side view of an ear cup 1100 of the air purifier 1000 of FIGS. 1a and 1b, whilst FIG. 3b shows a perspective view of an ear cup 1100 of the air purifier 1000 of FIGS. 1a and 1b. FIGS. 3a and 3b are then alternative cross-sectional views through the ear cup 1100 of FIG. 3a taken.

Each of the ear cups 1100 comprises a housing 1101 and an ear pad 1102 attached to the housing 1101, with the housing 1101 and the ear pad 1102 together defining a cavity 1103 having an opening 1104. A speaker or acoustic driver unit 1105 is then attached to the housing 1101 such that it is disposed within the cavity 1103. A feedforward microphone (i.e. a reference noise microphone) 1106 is then mounted to the housing 1101 such that it is acoustically coupled to the environment external to the housing 1101. Active noise control (ANC) circuitry 1107 is then connected to the both feedforward microphone 1106 and the acoustic driver 1105. This ANC circuitry 1107 is configured to use a feedforward signal 1170 provided by the feedforward microphone 1106 to operate the acoustic driver 1105 to attenuate noise having frequencies within a feedforward ANC range/interval, wherein this feedforward ANC range has a lower limit/minimum of at least (i.e. no less than) 300 Hz and an upper limit/maximum of more than 1.5 kHz. Specifically, the ANC circuitry 1107 comprises a feedforward filter that is configured to receive the feedforward signal 1170 as an input and to generate a feedforward filter output that causes the acoustic driver 1105 to attenuate noise having frequencies within the feedforward ANC range/interval.

Whilst the lower limit of the feedforward ANC range is at least 300 Hz, it is preferable that this lower limit is at least (i.e. no less than) 350 Hz and is more preferably approximately 500 Hz. Also, whilst the upper limit of the feedforward ANC range is more than 1.5 kHz, it is preferable that the upper limit of the feedforward ANC range is at least 2 kHz and is more preferably approximately 2 kHz. In a preferred embodiment, the lower limit of the feedforward ANC range is approximately 500 Hz and the upper limit is approximately 2 kHz.

In a more preferred embodiment, the ANC circuitry 1107 is configured to use a feedforward signal 1170 provided by the feedforward microphone 1106 to operate the acoustic driver 1105 to achieve one or more of attenuation of at least 5 dB at 2 kHz, attenuation of at least 10 dB between 350 Hz to 1.5 kHz, and attenuation of at least 15 dB between 500 Hz to 1 KHz.

Each of the ear cups 1100 further comprises a feedback microphone (i.e. an error noise microphone) 1108 disposed within the cavity 1103, adjacent to the acoustic driver 1105. The ANC circuitry 1107 is therefore also configured to use a feedback signal 1172 provided by the feedback microphone 1108 to operate the acoustic driver 1105 to attenuate noise having frequencies within a feedback ANC range/interval having an upper limit/maximum of no more than 1.5 kHz. Specifically, the ANC circuitry 1107 comprises a feedback filter that is configured to receive the feedback signal 1172 as an input and to generate a feedback filter output that causes the acoustic driver 1105 to attenuate noise having frequencies within the feedback ANC range.

Whilst the upper limit of the feedback ANC range is no more than 1.5 kHz, it is preferable that this upper limit is approximately 500 Hz. In addition, it is also preferable that the lower limit/minimum of the feedback ANC range is at least 20 Hz, and more preferably is approximately 50 Hz. In a preferred embodiment, the lower limit of the feedback ANC range is approximately 50 Hz and the upper limit is approximately 500 Hz.

In a more preferred embodiment, the ANC circuitry 1107 is therefore also configured to use a feedback signal 1172 provided by the feedback microphone 1108 to operate the acoustic driver 1105 to achieve one or more of attenuation of at least 5 dB between 50 Hz to 500 Hz, attenuation of at least 15 dB between 100 Hz to 300 Hz, and attenuation of at least 25 dB between 150 Hz to 250 Hz.

Each of the ear cups 1100 further comprises a motor-driven impeller 1109 disposed within the housing 1101 that is arranged to create an airflow through the housing 1101. The housing 1101 is therefore provided with an air inlet 1110 through which an airflow can be drawn into the housing 1101 by the motor-driven impeller 1109 and an air outlet 1111 for emitting the airflow from the housing 1101. A filter assembly 1112 is also disposed within the housing 1101 such that the airflow generated by the motor-driven impeller 1109 passes through the filter assembly 1112 and such that the airflow emitted from the ear cup 1100 is filtered/purified by the filter assembly 1112. The filter assembly 1112 is therefore located downstream (i.e. relative to the airflow generated by the impeller 1109) of the air inlet 1110 of the housing 1101 and upstream of the air outlet 1111. In the illustrated embodiment, the filter assembly 1112 is also located upstream relative to the motor-driven impeller 1109.

Each of the ear cups 1100 also comprises a motor control circuit 1107 that is arranged to control a rotational speed of a motor 1113 that drives the impeller 1109 such that the maximum rotational speed of the impeller 1109 is from 9000 to 18,000 RPM, is preferably from 10,000 to 14,000 RPM, and is more preferably from 10,000 to 12,000 RPM. As will be described below, it has been found these ranges of rotational speeds result in a fundamental frequency of the motor noise that can be attenuated by a conventionally configured feedback ANC system thereby improving the extent to which noise generated by the motor 1113 and/or the impeller 1109 can be cancelled out.

In the illustrated embodiment, the housing 1101 comprises a speaker chassis 1114 upon which the acoustic driver unit 1105 is mounted and a generally frusto-conical speaker cover 1115 mounted on the speaker chassis 1114 over the acoustic driver unit 1105. The speaker chassis 1114 comprises a generally circular base 1114a that is surrounded by a cylindrical side wall 1114b. The air outlet 1111 of the housing is then defined by an aperture formed in the cylindrical side wall 1114b. The ear cup 1100 is also provided with a hollow, rigid outlet duct 1130 that extends from the housing 1101 and that is arranged to connect the air outlet 1111 of the ear cup 1100 to an air inlet of the nozzle 1300.

A central portion of the base 1114a of the speaker chassis provides a driver support plate 1114c upon which the acoustic driver unit 1105 can be located. The generally frusto-conical speaker cover 1115 is then mounted on the speaker chassis 1114 over the entirety of the driver support plate 1114c such that the acoustic driver unit 1105 is covered by the speaker cover 1115. The driver support plate 1114c of the speaker chassis 1114 is provided with an array of apertures for allowing sound generated by the acoustic driver unit 1105 to pass through the speaker chassis 1114 into the cavity 1103 enclosed by ear pad 1102. In addition, the driver support plate 1114c is angled or tilted relative to the peripheral portion of the base 1114a of the speaker chassis 1114. The angle or tilt of the driver support plate 1114c is chosen so that the acoustic driver unit 1105 is substantially parallel with the ears when the head wearable air purifier 1000 is worn on the head of a user with the ear cup 1100 over the user's ear. For example, in the illustrated embodiment, the angle of the driver support plate 1114c relative to the peripheral portion of the base 1114a is from 10 to 15 degrees.

Figure 7:
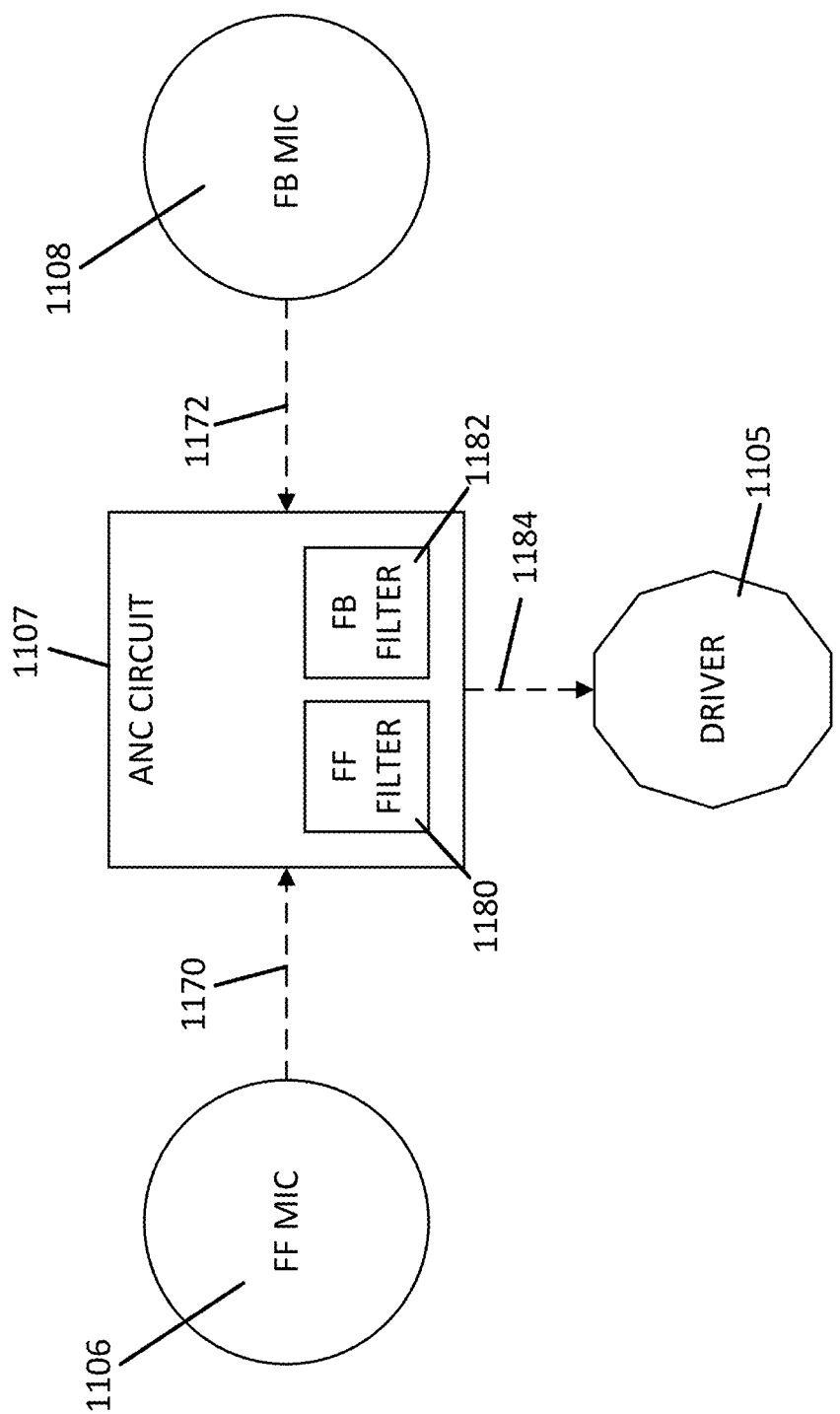
FIG. 7 is an exemplary implementation of an active noise control circuitry (ANC) according to the disclosure provided herein.

The feedback microphone 1108 is provided within the cavity 1103, adjacent to the acoustic transducer 1105, in order to acquire the sounds that are reaching the user so that any unwanted noise can be identified. Specifically, the feedback microphone 1108 is mounted on the speaker chassis 1114 between the acoustic transducer 1105 and the opening 1104 of the cavity 1103. The feedback microphone 1108 is arranged to provide data to the ANC circuitry 1107. As illustrated in FIG. 7, the ANC circuitry 1107 is provided by one or more processors that implement the feedforward ANC filter 1180 and the feedback ANC filter 1182 and that provide their output 1184 to an audio control circuit that is configured to control the audio transducer 1105.

In the illustrated embodiment, the ANC circuitry, the motor control circuit and the audio control circuit are provided by a single circuit board 1107 that is disposed on or mounted to the peripheral portion of the speaker chassis 1114. The circuit board 1107 therefore at least partially encircles the acoustic driver unit 1105 (i.e. is disposed outside/around a periphery of the acoustic driver unit 1105) when the acoustic driver unit 1105 is mounted on to the driver support plate 1114c.

A generally frusto-conical impeller casing 1116 containing both the impeller 1109 and the motor 1113 is then disposed over the speaker cover 1115 so that acoustic driver unit 1105 is nested within a recess or cavity defined by a back/rear of the impeller casing 1116. This impeller casing 1116 comprises a generally frusto-conical impeller housing 1117 surrounding the impeller 1109 and the motor 1113, and an annular volute 1118 fluidically connected to a base of the impeller housing 1117 and that is arranged to receive the air exhausted from the impeller housing 1117. The impeller housing 1117 is provided with an air inlet 1119 through which air can be drawn by the impeller 1109 and an air outlet 1120 through which the air is emitted from the impeller housing 1117 into the annular volute 1118. The air inlet 1119 of the impeller housing 1117 is provided by an aperture/opening at the small diameter end of the impeller housing 1117 and the air outlet 1120 is provided by an annular slot formed around a large diameter end or base of the impeller housing 1117.

The annular volute 1118 comprises a spiral (i.e. gradually widening) duct that is arranged to receive the air exhausted from the impeller housing 1117 and to guide the air to an air outlet 1121 of the volute 1118. The air outlet 1121 of the volute 1118 is then fluidically connected to the air outlet 1111 of the speaker assembly 1100. The term "volute" as used herein refers to a spiral funnel that receives the fluid being pumped by an impeller and increases in area as it approaches a discharge port. The air outlet 1121 of the volute 1118 therefore provides an efficient and quiet means for collecting the air that is exhausted from the circumferential annular slot that that forms the air outlet 1120 of the impeller housing 1117.

In the illustrated embodiment, the impeller 1109 is a mixed flow impeller that has a generally conical or frusto-conical shape. The impeller 1109 is hollow such that a rear/back side of the impeller 1109 defines a generally frusto-conical recess. The motor 1113 is then nested/disposed within this recess. Preferably, the impeller 1109 is a semi-open/semi-closed mixed flow impeller i.e. having a back shroud 1122 only. The back shroud 1122 of the impeller 1109 then defines the recess within which the motor 1113 is nested/disposed.

The impeller casing 1116 is then supported/suspended within the housing 1101 by a plurality of resilient supports 1123 that reduce the transmission of vibrations from the impeller casing 1116 to the speaker housing 1101. To do so, the plurality of resilient supports 1123 each comprise a resilient material such as an elastomeric or rubber material. In the illustrated embodiment, the only direct connection between the speaker housing 1101 and the impeller casing 1116 is provided by the resilient supports 1123.

The filter assembly 1112 is then mounted to the speaker chassis 1114 so that the filter assembly 1112 is provided upstream of the impeller 1109 and is arranged to be nested over the impeller casing 1116. The filter assembly 1112 comprises a filter seat 1124 supporting one or more filter elements 1125, 1126. In the illustrated embodiment, the filter assembly 1112 comprises both a particulate filter element 1125 and a chemical filter element 1126, with the particulate filter element 1125 located upstream relative to the chemical filter element 1126.

The filter seat 1124 is provided with a plurality of apertures 1127 that allow air to pass from a front surface of the filter seat 1124 to a rear/back surface of the filter seat 1124, with the front surface being arranged to support the filter elements 1125, 1126 over the plurality of apertures 1127. The filter seat 1124 then further defines an air passageway or channel 1128 between the rear/back surface of the filter seat 1124 and the air inlet 1119 of the impeller casing 1116 that is arranged to guide air to the air inlet 1119 of the impeller casing 1116. This air passageway 1128 is provided by a cavity defined between the rear/back surface of the filter seat 1124 and a front surface of the impeller casing 1116. Air must therefore pass through the filter elements 1125, 1126 before it can pass through the apertures 1127 in the filter seat 1124 and into the air passageway 1128 that leads to the air inlet 1119 of the impeller casing 1116.

In the illustrated embodiment, the filter seat 1124 is mounted to the speaker chassis 1114 and located over the impeller housing 1117, with the impeller housing 1117 partially disposed within a volume defined by a back of the filter seat 1124. In particular, the filter seat 1124 comprises a generally frusto-conical peripheral portion and a generally cylindrical central portion. The generally frusto-conical peripheral portion of the filter seat 1124 is provided with the plurality of apertures 1127 and is arranged to support one or more generally frusto-conical filter elements 1125, 1126 over the plurality of apertures 1127. The impeller housing 1117 is then at least partially disposed within the generally cylindrical central portion of the filter seat 1124. In particular, the air inlet 1119 of impeller housing 1117 is disposed within a volume defined by a back of the cylindrical central portion of the filter seat 1124.

The housing 1101 further comprises an outer cover 1129 that is mounted onto the speaker chassis 1114. This outer cover 1129 is arranged to fit over (and therefore generally conforms to) the filter assembly 1112 and is provided with an array of apertures that allow air to pass through the outer cover 1129 and that therefore define an air inlet 1110 of the outer cover 1129. These apertures are sized to prevent larger particles from passing through to the filter assembly 1112 and blocking, or otherwise damaging, the filter elements 1125, 1126. Alternatively, in order to allow air to pass through, the outer cover 1129 could comprise one or more grilles or meshes mounted within windows in the outer cover 1129. It will also be clear that alternative patterns of arrays are envisaged within the scope of the present invention.

The outer cover 1129 is releasably attached to the speaker chassis 1114 so as to cover the filter assembly 1112. For example, the outer cover 1129 could be attached to the speaker chassis 1114 using cooperating screw threads provided on the outer cover 1129 and the speaker chassis 1114 and/or using some catch mechanism. When mounted on speaker chassis 1114, the outer cover 1129 protects the filter elements 1125, 1126 from damage, for example during transit, and also provides a visually appealing outer surface covering the filter assembly 1112, which is in keeping with the overall appearance of the purifier 1000.

In the illustrated embodiment, the outer cover 1129 is provided as a hollow frustacone with open ends. The open large diameter end of the outer cover 1129 is arranged to fit over the periphery of the large diameter end of the filter assembly 1112, whilst the open small diameter end of the outer cover 1129 is arranged fit over both the periphery of the small diameter end of the filter assembly 1112 and the generally cylindrical central portion of the filter seat 1124. A circular front surface 1124a of the generally cylindrical central portion of the filter seat 1124 is therefore exposed within the open small diameter end of the outer cover 1129 and thereby forms a portion of the outer surface of the speaker assembly 1100. Preferably, the circular front surface 1124a of the filter seat 1124 is transparent and thereby forms a window through which the user to see the spinning of the impeller 1109 through the air inlet 1119 of the impeller casing 1116. This allows the user to visually check the speed of the impeller 1109 and to confirm that the impeller 1109 is functioning appropriately.

The feedforward microphone 1106 is provided adjacent to the outer surface of the housing 1101, towards the exterior of the ear cup 1100. Specifically, the feedforward microphone 1106 is mounted on the inner surface of the circular front surface 1124a of the filter seat 1124. The feedforward microphone 1106 is arranged to provide data to the ANC circuitry 1107, with the ANC circuitry 1107 then being configured to implement active noise cancellation (ANC) when controlling the acoustic driver unit 1105.

As shown in FIG. 1b, a first open end of the nozzle 1300 is connected to the rigid outlet duct 1130 that extends from the housing 1101 of the first speaker assembly 1100a. The nozzle 1300 then extends away from the first ear cup 1100a and assumes an arcuate shape so that the opposite, second open end of the nozzle 1300 connects to the rigid outlet duct 1130 that extends from the speaker housing 1101 of the second ear cup 1100b. The nozzle 1300 is arranged such that, when the purifier 1000 is worn by a user with the first ear cup 1100a over a first ear of the user and the second ear cup 1100b over a second ear of the user, the nozzle 1300 can extend around a face of the user, from one side to the other, and in front of a mouth of the user. In particular, the nozzle 1300 extends around the jaw of the user, from adjacent to one cheek to adjacent the other cheek, without making contact with the mouth, nose or surrounding regions of the user's face. It is therefore preferable that the at least a portion of the nozzle 1300 is formed of a transparent or partially transparent material so that the user's mouth is visible through the nozzle 1300 so as to avoid limiting the user's ability to clearly speak to others. For example, a central portion of the nozzle could be made from a flexible, transparent plastic such as a polyurethane, whilst the two end portions could each made from a stiff, transparent plastic such as a polyethylene terephthalate glycol-modified (PETG). Alternatively, the entire nozzle 1300 could be formed from a single transparent or partially transparent material.

The nozzle 1300 is provided with an air outlet 1301 for emitting/delivering the filtered air to a user. For example, the air outlet 1301 of the nozzle 1300 can comprise an array of apertures formed in a section of the nozzle 1300, with these apertures extending from an interior passage defined by the nozzle 1300 to an exterior surface of the nozzle 1300. Alternatively, the air outlet 1301 of the nozzle 1300 may comprise one or more grilles or meshes mounted within windows in the nozzle 1300.

In use, the purifier 1000 is worn by a user with the first ear cup 1100a over a first ear of the user and the second ear cup 1100b over a second ear of the user such that the nozzle 1300 can extend around a face of the user, from one ear to the other, and over at least the mouth of the user. Within each ear cup 1100a, 1100b, the rotation of the impeller 1109 by the motor 1113 will cause an airflow to be generated through the impeller casing 1116 that draws air into the speaker assembly 1100 through the apertures in the outer cover 1129. This flow of air will then pass through the filter elements 1125, 1126 disposed between the outer cover 1129 and the filter seat 1124 thereby filtering and/or purifying the airflow. The resulting filtered airflow will then pass through the apertures 1127 provided in the frustoconical portion of the filter seat 1124 into the air passageway 1129 provided by the space between the impeller casing 1116 and the opposing surface of the filter seat 1124, with the air passageway 1128 then guiding the airflow to the air inlet 1119 of the impeller casing 1116. The impeller 1109 will then force the filtered airflow out through the annular slot that provides the air outlet 1120 of the impeller housing 1117 and into the volute 1118 of the impeller casing 1116. The volute 1118 then guides the filtered airflow through the air outlet 1111 of the speaker assembly 1100, through the rigid outlet duct 1130 that extends from the housing 1101, and into the nozzle 1300 through an air inlet provided by one of the open ends of the nozzle 1300.

EXAMPLES

Measurements were taken for a head wearable purifier such as that described above using an artificial head measurement system equipped with microphones.

FIG. 4a shows the measurements taken with the motor on and without any ANC, whilst FIG. 4b shows the measurements taken with the motor on and whilst applying hybrid ANC. FIG. 4c then shows the attenuation achieved by the hybrid ANC on the internally originating noise arising from having the motor on (i.e. the difference between the measurements of FIGS. 4a and 4b) in comparison with the attenuation achieved by the hybrid ANC on externally originating noise (i.e. generated using an external speaker performing a frequency sweep). From this graph it can be seen that the hybrid ANC provides better attenuation of the externally originating noise at 150 Hz than the internally originating noise.

These measurements were repeated using the feedback ANC alone. FIG. 5a therefore shows the measurements taken with the motor on and without any ANC, whilst FIG. 5b shows the measurements taken with the motor on and whilst applying the feedback only ANC. FIG. 5c then shows the attenuation achieved by the feedback only ANC on the internally originating noise arising from having the motor on (i.e. the difference between the measurements of FIGS. 5a and 5b) in comparison with the attenuation achieved by the feedback only ANC on externally originating noise (i.e. generated using an external speaker performing a frequency sweep). From this graph it can be seen that the feedback only ANC provides almost the same level of attenuation for the externally originating noise as it does the internally originating noise arising from having the motor on.

Figure 6:
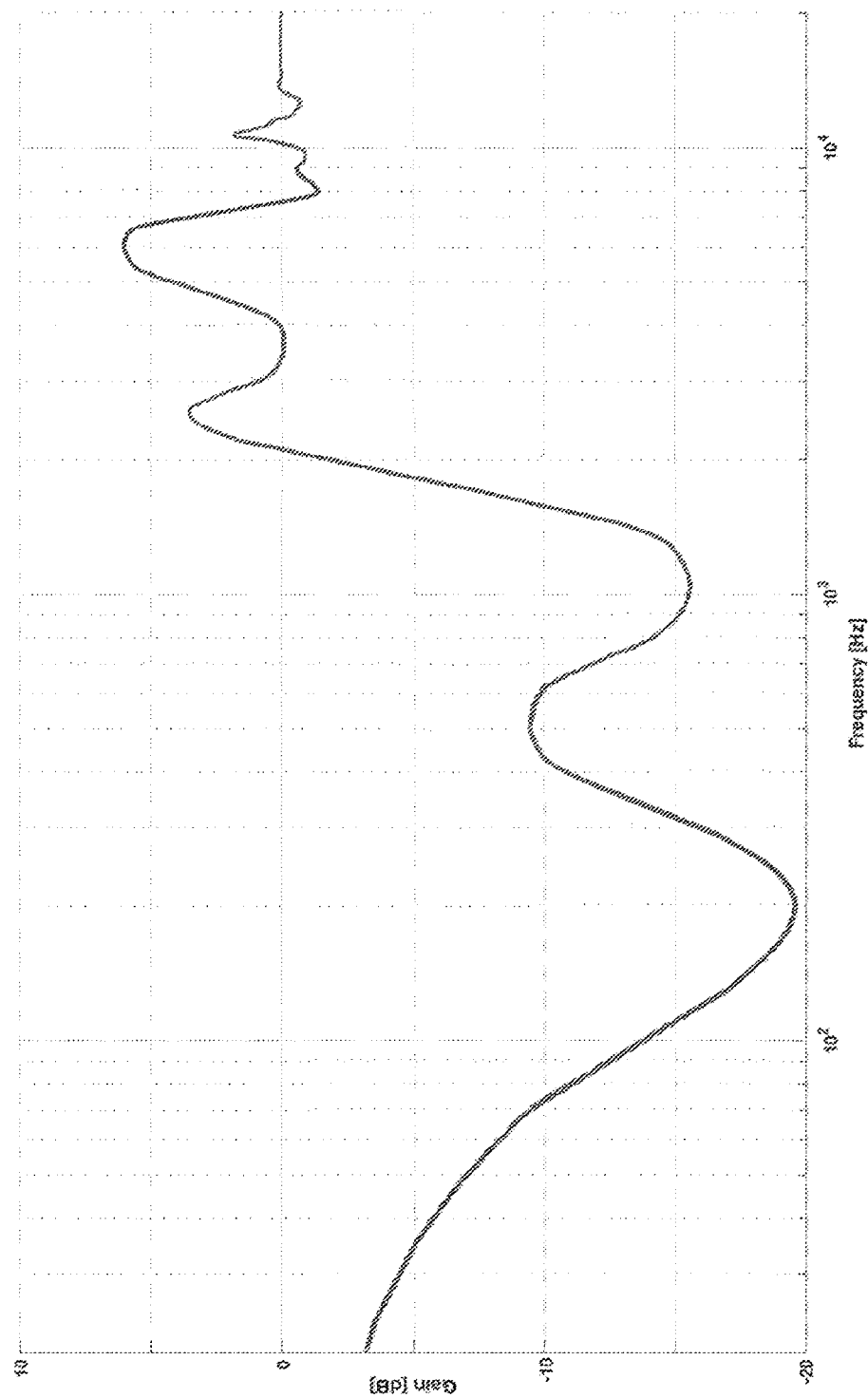
FIG. 6 is a graph showing an example of the response provided by a by hybrid active noise control that has been configured in accordance with the present invention.

From these results it was determined that the feedforward ANC does not achieve any further attenuation of the internally originating noise arising from having the motor on as the amount of motor noise that propagates from the external face of the ear cup is too low to add to the noise inside the ear cup. Consequently, the present inventors recognised that the feedback resources of a hybrid ANC system should be targeted at the fundamental frequency (1st harmonic) of the motor noise, and that the feedforward resources can therefore be tuned to deal with higher frequency noises such as the 6th harmonic of the motor noise and the more broadband air in-rush noise without amplifying the motor noise. Applying this approach to an example of a head wearable purifier such as that described above indicated that approximately 20 dB of attenuation at approximately 150 Hz could be achieved by appropriately tuning the feedback portion of the hybrid ANC system and that this would be sufficient to suppress the fundamental frequency (1st harmonic) of the motor noise, whilst the feedforward portion of the hybrid ANC system could be separately tuned to attenuate up to 10 dB or more of the noise in the frequency band 500 Hz to 2 kHz. An example of the response provided by a hybrid ANC system that is configured in this way is shown in FIG. 6.

It will be appreciated that individual items described above may be used on their own or in combination with other items shown in the drawings or described in the description and that items mentioned in the same passage as each other or the same drawing as each other need not be used in combination with each other. In addition, the expression "means" may be replaced by actuator or system or device as may be desirable. In addition, any reference to "comprising" or "consisting" is not intended to be limiting in any way whatsoever and the reader should interpret the description and claims accordingly.

Furthermore, although the invention has been described in terms of preferred embodiments as set forth above, it should be understood that these embodiments are illustrative only. Those skilled in the art will be able to make modifications and alternatives in view of the disclosure which are contemplated as falling within the scope of the appended claims. For example, in the above described embodiment the head wearable air purifier comprises a headphone system in which the two speaker assemblies are provided on opposite ends of a headband. However, the head wearable air purifier could equally comprise any head wearable article that could be used to support a first speaker assembly over a first ear of a user and a second speaker assembly over a second ear of the user. For example, the head wearable air purifier could comprise any type of headgear, such as a hat or a helmet, including safety hats and helmets, bicycle helmets, motorcycle helmets etc.

In addition, whilst in the above described embodiments both speaker assemblies include motor-driven impellers and filter assemblies, with both speaker assemblies then providing filtered/purified air to the nozzle, it is also possible that only one of the two speaker assemblies include a motor-driven impeller and a filter assembly, such that only a single speaker assembly then provides filtered/purified air to the nozzle. However, such an arrangement would not be as effective as those of the above described embodiments.

The invention claimed is:
1. An ear cup comprising:
a housing;
an ear pad attached to the housing and arranged such that the housing and the ear pad together define a cavity having an opening;
an acoustic driver disposed within the cavity;
a feedforward microphone carried by the housing and acoustically coupled to the environment external to the housing;
a feedback microphone disposed within the cavity;
a motor-driven impeller interposed between the feedforward microphone and the feedback microphone, the motor-driven impeller configured to generate an airflow through the housing; and
active noise control (ANC) circuitry that is configured to use measurements provided by the feedforward microphone to operate the acoustic driver to attenuate noise having frequencies within a feedforward ANC range having a lower limit and an upper limit such that the lower limit of the feedforward ANC range is approximately 500 Hz and the upper limit is approximately 2 kHz, and to use measurements provided by the feedback microphone to operate the acoustic driver to attenuate noise having frequencies within a feedback ANC range having an upper limit of no more than 500 Hz, wherein the feedback ANC range is configured to attenuate noise at a fundamental frequency of the motor-driven impeller, and the feedforward ANC range is configured to attenuate noise at a 6th harmonic frequency of the motor-driven impeller.

2. The ear cup of claim 1, wherein the active noise control circuitry is configured to receive the measurements from the feedforward microphone as an input and to generate an output that causes the acoustic driver to attenuate noise having frequencies within the feedforward ANC range.

3. The ear cup of claim 1, wherein the active noise control circuitry is configured to receive measurements from the feedback microphone as an input and to generate an output that causes the acoustic driver to attenuate noise having frequencies within the feedback ANC range.

4. The ear cup of claim 1, wherein the upper limit of the feedback ANC range is approximately 500 Hz.

5. The ear cup of claim 1, wherein the lower limit of the feedback ANC range is no less than 20 Hz.

6. The ear cup of claim 1, wherein the lower limit of the feedback ANC range is approximately 50 Hz and the upper limit is approximately 500 Hz.

7. The ear cup of claim 1, wherein a rotational speed of the motor-driven impeller is controlled such that the maximum rotational speed of the motor-driven impeller is from 9000 to 18,000 RPM.

8. The ear cup of claim 7, wherein the rotational speed of the motor-driven impeller is controlled such that the maximum rotational speed of the motor-driven impeller is from 10,000 to 14,000 RPM.

9. The ear cup of claim 1, wherein the housing comprises an air inlet through which an airflow can be drawn into the housing by the motor-driven impeller and an air outlet for emitting the airflow from the housing.

10. The ear cup of claim 1, and further comprising a filter assembly disposed within the housing, wherein the motor-driven impeller is arranged to create an airflow through the filter assembly.

11. The ear cup of claim 10, wherein the housing comprises an air inlet through which an airflow can be drawn into the housing by the motor-driven impeller and an air outlet for emitting the airflow from the housing and wherein the air outlet of the housing is downstream from the filter assembly.

12. The ear cup of claim 1, wherein the feedback ANC range does not overlap with the feedforward ANC range.

13. The ear cup of claim 12, wherein the housing comprises an air inlet through which an airflow can be drawn into the housing by the motor-driven impeller and an air outlet for emitting the airflow from the housing.

14. The ear cup of claim 12, and further comprising a filter assembly disposed within the housing, wherein the motor-driven impeller is arranged to create an airflow through the filter assembly.

15. The ear cup of claim 1, wherein the ear cup is configured as any of a circumaural ear cup and a supra-aural ear.

16. A head wearable device comprising: a headgear; and the ear cup of claim 1, wherein the ear cup is attached to the headgear and is arranged to be worn over an ear of a user.

17. The head wearable device of claim 16, and further comprising a further ear cup arranged to be worn over a further ear of the user.

18. The head wearable device of claim 17, wherein the further ear cup is an ear cup comprising:
a housing;
an ear pad attached to the housing and arranged such that the housing and the ear pad together define a cavity having an opening;
an acoustic driver disposed within the cavity;
a feedforward microphone carried by the housing and acoustically coupled to the environment external to the housing;
a feedback microphone disposed within the cavity; and
active noise control (ANC) circuitry that is configured to use measurements provided by the feedforward microphone to operate the acoustic driver to attenuate noise having frequencies within a feedforward ANC range having a lower limit of and an upper limit such that the lower limit is greater than 300 Hz and the upper limit is greater than 1.5 kHz, and to use measurements provided by the feedback microphone to operate the acoustic driver to attenuate noise having frequencies within a feedback ANC range having an upper limit of no more than 500 Hz.

19. A head wearable device of claim 16, wherein the headgear comprises a headband arranged to be worn on the head of a user, and the ear cup is mounted on a first end of the headband and the further ear cup is mounted on an opposite, second end of the headband.

20. The ear cup of claim 1, wherein the lower limit of the feedback ANC range is approximately 50 Hz and the upper limit is approximately 500 Hz, and the feedback ANC range does not overlap with the feedforward ANC range.

* * * * *